United States Patent
Schelch et al.

(10) Patent No.: US 11,981,587 B2
(45) Date of Patent: May 14, 2024

(54) DISINFECTION DEVICE AND METHOD FOR PERFORMING DISINFECTION CYCLES

(71) Applicants: Michael Schelch, Oberaich (AT); Wolfgang Staber, Bruck an der Mur (AT)

(72) Inventors: Michael Schelch, Oberaich (AT); Wolfgang Staber, Bruck an der Mur (AT)

(*) Notice: Subject to any disclaimer, the term of this patent is extended or adjusted under 35 U.S.C. 154(b) by 1025 days.

(21) Appl. No.: 16/777,620

(22) Filed: Jan. 30, 2020

(65) Prior Publication Data

US 2021/0238066 A1    Aug. 5, 2021

(51) Int. Cl.
*C02F 1/46* (2023.01)
*A61F 7/00* (2006.01)
*C02F 1/461* (2023.01)
*C02F 1/467* (2023.01)

(52) U.S. Cl.
CPC .............. *C02F 1/4672* (2013.01); *A61F 7/00* (2013.01); *C02F 1/46109* (2013.01); *A61F 2007/0056* (2013.01); *C02F 2001/46147* (2013.01); *C02F 2201/46125* (2013.01); *C02F 2201/46145* (2013.01); *C02F 2201/4617* (2013.01); *C02F 2303/04* (2013.01)

(58) Field of Classification Search
CPC ...... C02F 1/46; C02F 1/32; C02F 1/36; A61F 7/00

See application file for complete search history.

(56) References Cited

U.S. PATENT DOCUMENTS

2017/0005779 A1* 1/2017 Rowland ............... H04L 7/0008
2017/0348449 A1* 12/2017 Ward ..................... A61L 2/24

FOREIGN PATENT DOCUMENTS

| CA | 2495044 A1 * | 7/2005 | ............ C02F 1/4674 |
| CN | 101405013 A * | 4/2009 | ............. A61K 33/00 |
| CN | 105246837 A * | 1/2016 | ............. B63J 4/002 |
| DE | 10 2017 000 426 A1 | 7/2018 | |
| DE | 102017000426 A1 * | 7/2018 | |
| WO | WO-2017135208 A1 * | 8/2017 | ............... C02F 1/46 |

OTHER PUBLICATIONS

DE-102017000426-A1, Jul. 2018; country DE; Bongert M, English translation (Year: 2018).*
CN-101405013-A; Apr. 2009; Country CN; Alimi H, English translation (Year: 2009).*

(Continued)

*Primary Examiner* — Walter D. Griffin
*Assistant Examiner* — Cameron J Allen
(74) *Attorney, Agent, or Firm* — Maschoff Brennan

(57) ABSTRACT

A disinfection device for performing disinfection cycles of water from at least one water circuit of an apparatus, in particular a heating/cooling device. The disinfection device includes at least one disinfection circuit for passing through the water from the water circuit having at least one electrolysis cell designed as a flow-through cell for the in situ generation of oxidizing agents. The water circuit is connected to the disinfection circuit to form a common circuit. Electronics control the disinfection cycles. Power is supplied to the components of the provided disinfection circuits.

17 Claims, 2 Drawing Sheets

(56) References Cited

OTHER PUBLICATIONS

DE 102005049951 B4; Apparatus for the Preparation of Physiological, Therapeutic and Chemotherapeutic Aqueous Rinsing Solutions, with translation, Becker Franz Ferdinand; May 13, 2015 (Year: 2015).*
KR 100947256 B1; Electrolysis Apparatus for Water Treatment, with translation, Shin Hyun Su Mar. 11, 2010 ( Year: 2010).*
DE 102017000426 A1; Method and Disinfection Device for Disinfecting Fluid Circuits in a Device, in Particular for Water Circuits in a Hypothermia Device, with translation, Bongert Markus; Jul. 19, 2018 (Year: 2018).*
English translation of Electrolyzed Water Generation Device and Electrolyzed Water Server Comprising Same; WO 2017135208 A1, Tachibana Takahito, Jan. 31, 2017 (Year: 2017).*
English translation of Manufacture of Neutral Electrolyzed Water for Sterilization, Involves Electrolyzing To-be-processed Water Containing Specific Salt and Water Using Direct Current or Pulse Current With Preset Voltage and Current Density, WO 2006041001 A1, Omasa (Year: 2006).*
English translation of Water Treatment System, CN 105246837 A; 2014 Park, Kyu-Won (Year: 2014).*
English translation of an Intelligent Water Fountain Capable of Sterilizing; CN 204862670 U, Dec. 16, 2015, Li, Xue-bo (Year: 2015).*

* cited by examiner

DISINFECTION DEVICE AND METHOD FOR PERFORMING DISINFECTION CYCLES

BACKGROUND

The invention relates to a disinfection device for performing disinfection cycles of water from at least one water circuit of an apparatus, in particular a heating/cooling device. The invention further relates to a method for performing disinfection cycles of water in at least one water circuit of an apparatus, in particular a heating/cooling device, in a disinfection circuit of a disinfection device, the water circuit being connected to the disinfection circuit into a common circuit and the water being pumped out of the water circuit through the disinfection circuit.

In order to avoid the risk of infections after operations, for example, cardiac surgery, extensive measures which involve considerable technical and organizational effort are taken in the operating theaters. In the case of open-heart surgery, for example, the patient must be connected to a heart-lung machine, wherein his blood is oxygenated and decarboxylated in an extracorporeal circuit for the duration of the operation. The blood temperature must be regulated at the same time to prevent the patient from cooling down. The blood is temperature controlled by means of a heat exchanger, the heat transfer medium of which is water, which is correspondingly temperature controlled in a heating/cooling device. Heating/cooling devices are known to be mobile, multi-circuit heating-cooling devices that are independent of water connections and are mostly used for the controlled temperature control of two water circuits during extracorporeal perfusion for the controlled temperature control of the patient and the cardioplegia circuit using heat exchangers. It is known that in heating/cooling devices, the heat transfer liquid water is contaminated with germs relatively quickly in practice and a biofilm forms on the wetted inner surface of the lines and tanks in the heating/cooling device. Germ contamination and the formation of biofilms usually occur even when the heating/cooling device has been cleaned in accordance with the maintenance schedule. If contaminated water unintentionally escapes from a water circuit of the heating/cooling device, there is a risk of serious post-operative infections of the patient.

A disinfection device and a method of the type mentioned above are known from DE 10 2017 000 426 A1. The water of the water circuits is passed for disinfection at least temporarily through a disinfection apparatus which has an apparatus for providing a disinfection fluid. The disinfection fluid is added to the liquid that is passed through, and the water is disinfected by the disinfection fluid in a deactivation unit. The disinfected liquid is then passed into an elimination unit for eliminating the disinfection fluid, in which the disinfected liquid remains or passes through until the disinfection fluid is completely removed from the disinfected liquid by the elimination unit. Ozone is preferably used as a disinfection fluid. UV radiation is used in the elimination unit to decompose and break down the disinfection fluid after the liquid has been disinfected.

Furthermore, it is widespread and customary to add oxidizing agents, for example, hydrogen peroxide, to the water in heating/cooling devices approximately every two to three weeks. Handling such means poses certain health risks and is increasingly discredited for reasons of employee protection.

SUMMARY

The invention has for its object to provide a disinfection device and a method which ensures, in a technically simple and particularly reliable manner, a sterilization of the process water from heating/cooling devices without the separate use of disinfectants and therefore without the need to eliminate the same. A comfortable and uncomplicated commissioning should thereby be possible and frequent water changes in the heating/cooling device can be dispensed with.

According to the invention, the object is achieved using a disinfection device having
  i. at least one disinfection circuit for passing through the water from the water circuit having at least one electrolysis cell designed as a flow-through cell for the in situ generation of oxidizing agents,
  ii. means for connecting the water circuit to the disinfection circuit to form a common circuit,
  iii. electronics (8) for controlling the disinfection cycles and
  iv. means for supplying power to the components of the provided disinfection circuits.

In the method according to the invention, the water is passed in the disinfection circuit through an electrolysis cell designed as a flow-through cell, in which oxidizing agents are generated in electrochemical reactions and in situ, and
is pumped several times within a disinfection cycle through the circuit formed by the water circuit and the disinfection circuit.

The method according to the invention and the device according to the invention enable a disinfection and sanitization of the water from the water circuits of the heating/cooling device without the separate addition of disinfectants, since the disinfectants are generated directly in the electrolysis cell when the water to be disinfected flows through. The repeated flow through the electrolysis cells ensures that the impurities in the water are safely broken down and only small amounts of unstable oxidizing radicals remain in the water, which radicals remove themselves. The water is therefore disinfected on the basis of in situ ongoing electrochemical processes through water electrolysis. This also ensures a comfortable and uncomplicated commissioning of the disinfection device, since all that is required is to couple the hoses of the water circuits of the heating/cooling device to the disinfection device and to start the disinfection cycle.

In a preferred embodiment of the disinfection device, this has a pump in each disinfection circuit for repeatedly passing the water through the water circuit and the disinfection circuit within a disinfection cycle. Depending on the embodiment of the heating/cooling device, a circulation pump can also be used within the heating/cooling device to pump water through the disinfection circuit in the disinfection device and the water circuit in the heating/cooling device. A separate pump in the disinfection device can be omitted in this case.

A flow sensor and in particular also a temperature measurement sensor are also preferably further present in each disinfection circuit. Preferably a sensor for measuring the electrical conductivity is a further component per disinfection circuit. The measurement data of at least one of these sensors are taken into account in the electronics for controlling the disinfection cycles.

In a preferred embodiment the electronics control a disinfection cycle taking into account measured data, such as the water temperature and the flow rate.

In a preferred, simple embodiment of the disinfection device, empirically determined data from experiments are taken into account in the electronics for controlling the disinfection cycles. In particular, the number of passes of the water through the flow-through cell required to generate a sufficient quantity of oxidizing agents for disinfection is determined in such experiments. Alternatively, at least one further sensor can be positioned in each disinfection circuit, which sensor measures the concentration of oxidizing agent in the water, so that the electronic controller processes these measurement data and controls the disinfection cycle on the basis of this data.

The flow-through cell preferably has an electrode packet having two edge-side contact electrodes, which are supplied with DC voltage, and in a preferred embodiment, at least one bipolar electrode which is arranged between the contact electrodes and spaced therefrom. The bipolar electrode is in particular a diamond particle electrode which has doped, preferably boron-doped, diamond particles which are embedded in one layer and without mutual contact with one another in a non-conductive plastic carrier layer and are exposed on both sides of said carrier layer. Flow cells of this type are particularly effective with regard to the generation of oxidizing agents from the water or its constituents by means of electrochemical processes.

The disinfection device is preferably designed as an additional device for a heating/cooling device, can be positioned on the heating/cooling device and can be connected thereto.

In the method for performing disinfection cycles, the water is pumped in an electronically controlled manner through the water circuit and the disinfection circuit within a disinfection cycle until it is safely disinfected. As already mentioned, the electronics control a disinfection cycle based on certain data or measured values, such as the water temperature and the flow rate.

The method is particularly effective when the water to be disinfected is at least largely free of hardeners. It is therefore advantageous to use water in the heating/cooling device which is at least largely free of hardeners, for example, by suitable additives or by treatment in an osmosis device.

For the electrochemical processes in the electrolysis cell, it is particularly advantageous when the water to be disinfected has an electrical conductivity of at least 1 mS/cm. This is achieved in a particularly simple manner in that at least one salt, for example, NaCl, KCl, $K_2SO_4$, $Na_2SO_4$, $K_2CO_3$ and/or $NA_2CO_3$, is dissolved in the disinfecting water. Such salts can be mixed in or added in a simple manner when filling the water into the heating/cooling device.

BRIEF DESCRIPTION OF DRAWINGS

Further features, advantages and embodiments of the invention are now described in more detail with reference to the drawing, which illustrates an embodiment. Shown are FIG. 1 a schematic structure of a disinfection device, FIGS. 2 and 3 views of an embodiment of an electrolysis cell designed as a flow-through cell and FIG. 4 a sectional representation along the sectional plane marked line in FIG. 1.

DETAILED DESCRIPTION

Figure 1:
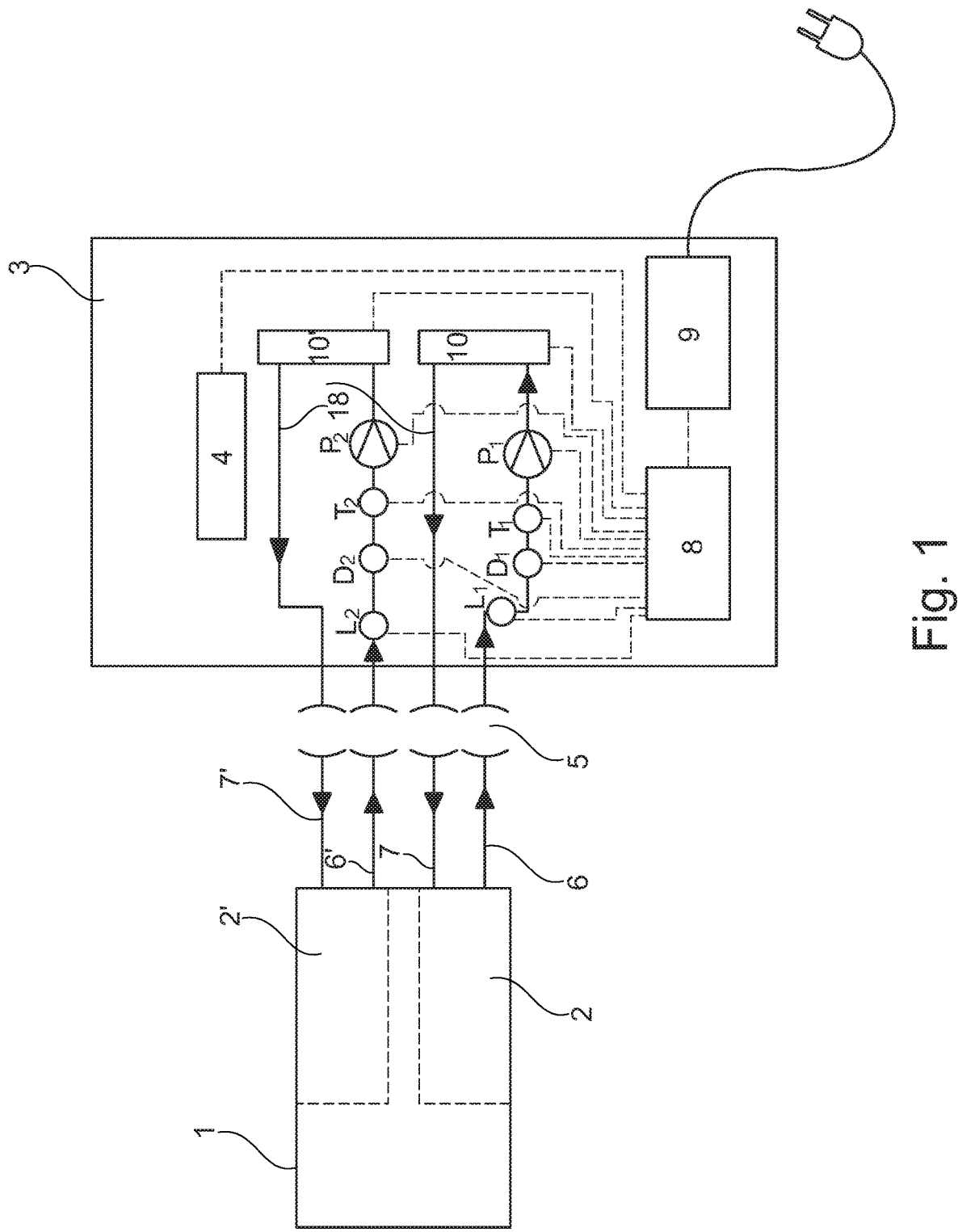

FIG. 1 schematically shows the structure of an embodiment of a disinfection device according to the invention as an additional device, in particular for a heating/cooling device 1. The heating/cooling device 1 is a multi-circuit heating-cooling device for the controlled temperature control of independent water circuits and can be any heating/cooling device from the prior art. The heating/cooling device indicated in FIG. 1 works, for example, with two independent water circuits, such as a patient circuit and a cardioplegia circuit, and therefore contains two water tanks 2, 2' indicated in FIG. 1. In order to prevent the process water from becoming contaminated and the associated formation of biofilms on the tank walls and the walls of the hose lines through which the process water flows, the process water should in particular be disinfected daily.

The disinfection device according to the invention is placed on the heating/cooling device 1 and is preferably fixed using mounting brackets or the like provided therefor. The disinfection device therefore has a correspondingly designed housing 3, which is only indicated in FIG. 1, on the outside of the housing 3 couplings 5 for connecting to the ends of the hoses 6, 6' and 7, 7' of the heating/cooling device 1 and a display 4 having control elements and display elements. The display 4 and the couplings 5 are only indicated in FIG. 1. The couplings 5 are marked or designated accordingly so that the inlet hoses 6, 6' and return hoses 7, 7' belonging to the two water circuits of the heating/cooling device 1 on the disinfection device can be connected to the correct or assigned couplings.

The disinfection device shown in the example according to FIG. 1 contains two disinfection circuits corresponding to the number of water circuits of the heating/cooling device 1. The two disinfection circuits each have, in the flow direction of the water to be disinfected, a flow sensor D1, D2 for measuring the flow, a temperature measurement sensor T1, T2, a pump P1, P2 and an electrolysis cell designed as a flow-through cell 10, 10' and connecting hoses 18.

In an alternative embodiment, the disinfection device has a single disinfection circuit matched to the heating/cooling device. Furthermore, instead of or in addition to the pump provided in the disinfection circuit, a circulation pump which may be present in the heating/cooling device can be used.

Flow sensors $L_1$ and $L_2$ are optionally provided in the disinfection circuits, in particular in front of sensors $D_1$ and $D_2$, for measuring the conductivity of the water flowing through. The sensors $D_1$, $D_2$, $L_1$, $L_2$, $T_1$, $T_2$, the pumps $P_1$, $P_2$ and the two flow-through cells 10, 10' are connected to electronics 8 for controlling the disinfection cycles. The electronics 8 and the individual components of the disinfection device are supplied with voltage via a power supply unit 9.

Figure 2:
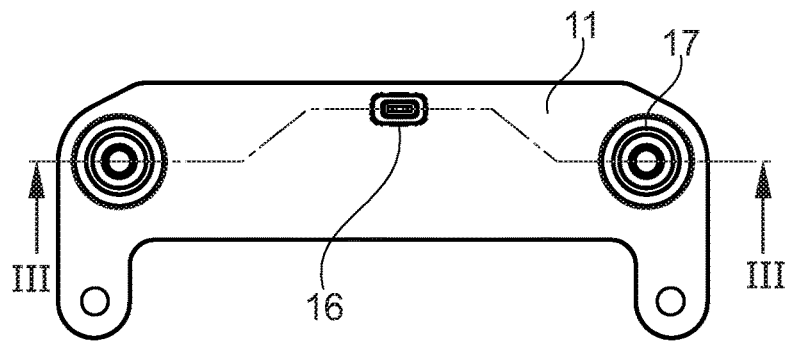
Figure 3:
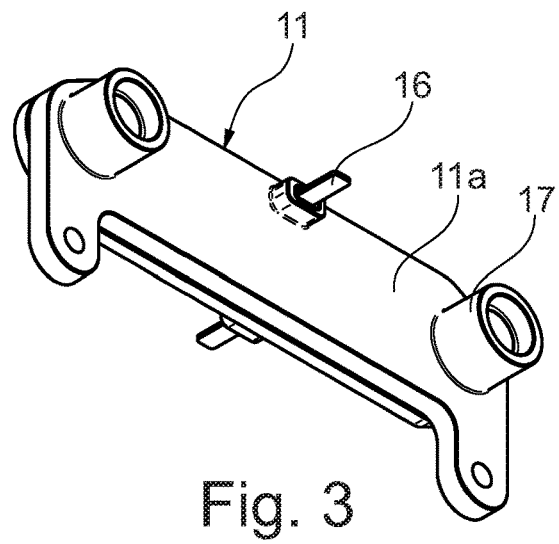
Figure 4:
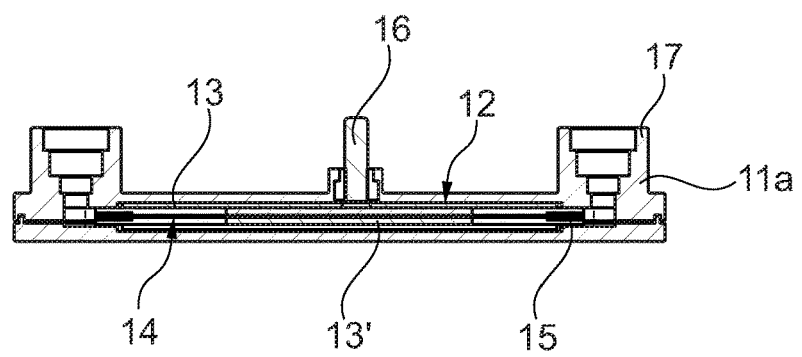

FIGS. 2 to 4 illustrate the structure of an embodiment of a flow-through cell 10, 10'. Every flow-through cell 10, 10' has a housing 11 made of two housing parts 11a which are firmly connected to one another, in particular welded to one another. In the housing 11 is located an electrode packet 12 having two edge-side contact electrodes 13, 13' and a bipolar electrode 14, in particular a diamond particle electrode, located between the contact electrodes 13, 13'. Each frame-like spacer 15 made of electrically insulating material separates the two contact electrodes 13, 13' from the bipolar central electrode 14. All electrodes 13, 13' and 14 are, in particular, thin, rectangular plates having essentially matching dimensions.

The edge-side contact electrodes 13, 13' consist, for example, of platinum-coated or mixed oxide-coated titanium, of diamond electrodes produced by means of CVD technology, or of another electrochemically stable electrode material. The spacers 15 consist of a chemically resistant, electrically non-conductive plastic, for example, PP (polypropylene), PVDF (polyvinylidene fluoride) or PTFE (polytetrafluoroethylene). The diamond particle electrode 14 is in particular a conventional diamond particle electrode as is known, for example, from EP 2 004 880 B1. This diamond particle electrode consists of doped diamond particles, which are embedded in one layer and without mutual contact with one another in a non-conductive plastic carrier layer and are exposed on both sides of said carrier layer. The electrical contacting of the contact electrodes 13, 13' takes place, for example, on the contact tabs 16 which are formed with the contact electrodes 13, 13' and which are guided liquid-tight through the housing 11 outwards by means of a seal or a sealing material. The housing 11 is further provided with two connections 17 having flow openings, to which the hoses 18 running inside the disinfection device and connecting the individual components to one another are connected.

The means for disinfection of the water are generated in the operation of the respective disinfection circuit or in the operation of the flow-through cell 10, 10' in the flow-through cell 10, 10' by electrochemical conversion of the water itself or of introduced water constituents. In particular, OH radicals are generated at the electrodes, which radicals oxidize organic components in the water or react with salts dissolved in the water and generate oxidizing agents. Oxidizing agent mixtures which neutralize the impurities contained in the water are therefore formed in the in situ operation of the flow-through cell 10, 10'.

In order to prevent the formation of deposits, for example, lime, in the components of the water circuits of the heating/cooling device and the disinfection circuits of the disinfection device, it is advantageous to use water that is free or largely free of hardeners such as calcium or magnesium in the heating/cooling device. Such water is, for example, produced using a softening or reverse osmosis system. The water should further have a certain electrical conductivity on the order of at least 1 mS/cm, so that the formation of oxidizing agents is supported in the flow-through cells 10, 10'. At least one salt, for example, NaCl, KCl, $K_2SO_4$, $Na_2SO_4$, $K_2CO_3$ and/or $NA_2CO_3$, is therefore added to the water when it is filled into the water tanks 2, 2' of the heating/cooling device 1. These salts can be provided in the form of powder or tablets. The amount of salt to be added depends on the known water volume.

Both disinfection circuits can perform a disinfection cycle simultaneously or in succession when operating the disinfection device. The electronics 8 that can be operated via the display 4 can provide both options as alternatives. In the course of a disinfection cycle, the water is conveyed from one of the tanks 2, 2' several times via the pumps P1, P2 through the water circuits of the heating/cooling device and the disinfection circuits of the disinfection device and thus passes through the respective flow-through cell 10, 10'. A common disinfection process having a water volume of eight liters, for example, requires about five minutes. An acoustic or visual signal can indicate the termination of the disinfection process. The electronic controller works in particular on the basis of the results of empirical experiments and taking into account known and available data, such as that of the water temperature and the flow rate. Alternatively or additionally, the electronics control the disinfection cycles on the basis of measurement data from at least one sensor which detects the concentration of oxidizing agent in the water, for example, the concentration of free chlorine, or which measures the redox potential.

In alternative embodiments of the flow-through electrode, said flow-through electrode has only two contact electrodes and no bipolar electrode, in a further alternative embodiment, two or three bipolar electrodes can be provided in the electrode pack.

REFERENCE NUMBER LIST

1 . . . heating/cooling device
2, 2' . . . water tank
3 . . . housing
4 . . . display
5 . . . coupling
6, 6' . . . circulation hose
7, 7' . . . return hose
8 . . . electronics
9 . . . power supply unit
10, 10' . . . flow-through cell
11 . . . housing
11a . . . housing part
12 . . . electrode pack
13, 13' . . . contact electrode
14 . . . bipolar electrode
15 . . . spacers
16 . . . contact tab
17 connection
18 . . . hose
$D_1$, $D_2$ . . . flow sensor
$L_1$, $L_2$ . . . conductivity sensor
$P_1$, $P_2$ . . . pump
$T_1$, $T_2$ . . . temperature measuring sensor

The invention claimed is:

1. A disinfection device for performing disinfection cycles of water from at least one water circuit of a heating/cooling device, comprising:
   at least one disinfection circuit through which the water from the water circuit of the heating/cooling device passes through,
   means for detachably connecting the water circuit located in the heating/cooling device to the at least one disinfection circuit to establish a common and self-contained water circuit;
   at least one electrolysis cell installed in the disinfection circuit and designed as a flow-through cell, the electrolysis cell configured to generate oxidizing agents in situ as the water from the water circuit of the heating/cooling device flows through the disinfection circuit, wherein the flow-through cell has an electrode packet having two edge-side contact electrodes supplied with DC voltage and at least one bipolar electrode which is arranged between the two edge-side contact electrodes and spaced therefrom;
   means for connecting the water circuit to the disinfection circuit to form the common circuit;
   electronics for controlling a number of the disinfection cycles until the water from the water circuit of the heating/cooling device is disinfected; and
   means for supplying power to components of the provided disinfection circuits.

2. The disinfection device according to claim 1, further comprising a pump for repeatedly passing the water through the water circuit and the disinfection circuit within a disinfection cycle.

3. The disinfection device according to claim 1, further comprising a flow measurement sensor for the disinfection circuit.

4. The disinfection device according to claim 1, further comprising a temperature measurement sensor for the disinfection circuit.

5. The disinfection device according to claim 1, further comprising a sensor for measuring the electrical conductivity for the disinfection circuit.

6. The disinfection device according to claim 1, further comprising a housing having a display having control elements and display elements.

7. The disinfection device according to claim 1, wherein the electronics control a disinfection cycle taking into account measured data, the measuring data including at least one of water temperature and flow rate.

8. The disinfection device according to claim 1, wherein the electronics control a disinfection cycle on the basis of empirically determined data from experiments and/or measurement data from at least one sensor which measures the concentration of oxidizing agent in the water.

9. The disinfection device according to claim 1, wherein the bipolar electrode is a diamond particle electrode which has doped diamond particles which are embedded in one layer and without mutual contact with one another in a non-conductive plastic carrier layer and are exposed on both sides of said carrier layer.

10. The disinfection device according to claim 1, wherein the disinfection device is capable of being used with and connected with a heating/cooling device.

11. A method for performing disinfection cycles of water of at least one water circuit of a heating/cooling device, in a disinfection circuit of a disinfection device, the method comprising:
   connecting the disinfection device to the heating/cooling device to establish a common water circuit composed of the water circuit of the heating/cooling device and the disinfection circuit of the disinfection device, the water of the at least one water circuit including electrical conductivity of at least 1 mS/cm;
   by a pump installed in the disinfection circuit of the disinfection device, pumping the water a plurality of times within a disinfection cycle through the common circuit formed by the water circuit and the disinfection circuit; and
   within the disinfection circuit, passing the water through an electrolysis cell installed in the disinfection circuit and designed as a flow-through cell that operates in the common circuit with the water circuit, the electrolysis cell configured to generate oxidizing agents in electrochemical reactions and in situ as the water from the water circuit flows through the electrolysis cell,
   wherein the flow-through cell has an electrode packet having two edge-side contact electrodes supplied with DC voltage and at least one bipolar electrode which is arranged between the two edge-side contact electrodes and spaced therefrom, and
   an electronic control is provided which pumps the water through the common water circuit within a disinfection cycle until it is disinfected.

12. The method according to claim 11, wherein the temperature and the flow rate of the water are measured in the disinfection circuit.

13. The method according to claim 11, wherein the disinfection cycle is controlled electronically such that the water is pumped through the water circuit and the disinfection circuit within a disinfection cycle until it is safely disinfected.

14. The method according to claim 11, wherein the disinfection cycle is controlled taking into account measured data, the measuring data including at least one of water temperature and flow rate.

15. The method according to claim 11, wherein the disinfection cycle is controlled taking into account empirically determined data from experiments and/or measurement data from at least one sensor which measures the concentration of oxidizing agent in the water.

16. The method according to claim 11, wherein in that the water to be disinfected is at least largely free of hardeners.

17. The method according to claim 11, wherein at least one salt is dissolved in the water to be disinfected.

* * * * *